United States Patent
Mitra et al.

(10) Patent No.: US 9,452,127 B2
(45) Date of Patent: *Sep. 27, 2016

(54) SURFACTANT-FREE ORGANOPOLYSILOXANE INVERT EMULSIONS

(71) Applicant: Wacker Chemical Corporation, Adrian, MI (US)

(72) Inventors: Amitabha Mitra, Saline, MI (US); Michael Coffey, Adrian, MI (US); Christine Klingler, Pittsford, MI (US)

(73) Assignee: WACKER CHEMICAL CORPORATION, Adrian, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/152,165

(22) Filed: Jan. 10, 2014

(65) Prior Publication Data

US 2015/0196481 A1 Jul. 16, 2015

(51) Int. Cl.

| | |
|---|---|
| *A61K 8/893* | (2006.01) |
| *A61K 8/894* | (2006.01) |
| *A61Q 1/00* | (2006.01) |
| *A61Q 5/00* | (2006.01) |
| *C08L 83/12* | (2006.01) |
| *C09K 3/18* | (2006.01) |
| *A61K 8/06* | (2006.01) |
| *A61Q 1/04* | (2006.01) |
| *C08G 77/46* | (2006.01) |
| *C08G 77/00* | (2006.01) |

(52) U.S. Cl.
CPC ............. *A61K 8/893* (2013.01); *A61K 8/064* (2013.01); *A61K 8/894* (2013.01); *A61Q 1/00* (2013.01); *A61Q 1/04* (2013.01); *C08L 83/12* (2013.01); *C09K 3/18* (2013.01); *A61K 2800/21* (2013.01); *A61K 2800/33* (2013.01); *A61K 2800/594* (2013.01); *C08G 77/46* (2013.01); *C08G 77/80* (2013.01)

(58) Field of Classification Search
None
See application file for complete search history.

(56) References Cited

U.S. PATENT DOCUMENTS

| | | | |
|---|---|---|---|
| 4,532,132 | A | 7/1985 | Keil |
| 4,698,178 | A | 10/1987 | Huettinger et al. |
| 5,643,555 | A | 7/1997 | Collin et al. |
| 5,853,711 | A | 12/1998 | Nakamura et al. |
| 6,379,680 | B2 | 4/2002 | Gers-Barlag et al. |
| 6,391,321 | B1 | 5/2002 | Gers-Barlag et al. |
| 7,914,772 | B2 | 3/2011 | Polonka et al. |
| 8,524,262 | B2 | 9/2013 | Roy et al. |
| 2012/0028308 | A1 | 2/2012 | Keller et al. |
| 2012/0213721 | A1* | 8/2012 | Roy et al. ................ 424/64 |

FOREIGN PATENT DOCUMENTS

| | | |
|---|---|---|
| EP | 1 035 154 A2 | 9/2000 |
| WO | 00/69423 A1 | 11/2000 |
| WO | 2012013648 A1 | 2/2012 |
| WO | 2012/113714 A1 | 8/2012 |
| WO | 2012/145862 A1 | 11/2012 |

OTHER PUBLICATIONS

PCT/US2004/040603, International Filing Date Jun. 12, 2004, Applicant: Ashland, Inc., "Cleaning and Polishing Wax Composition", pp. 1-21.
U.S. Appl. No. 11/699,906, filed Jan. 30, 2007, "Silicone Based Emulsions for Topical Drug Delivery", pp. 1-34, Inventor: Gareth Winckle (now abandoned).
U.S. Appl. No. 13/755,135, filed Jan. 31, 2013, "Amphiphilic Organopolysiloxane Dendrimers With High Refractive Index", pp. 1-22, Application: Wacker Chemical Corporation.
http://www.makingcosmetics.com/articles/27-how-to-make-water-in-oil-emulsions.pdf (n.d.). Retrieved Oct. 3, 2013, from www.makingcosmetics.com.
Klein, K. "Formulating Water-In-Oil Emulsions: A Scary Endeavor", Cosmetics & Toiletries Magazine, vol. 118, No. 10, Oct. 2003, pp. 24-25.

* cited by examiner

*Primary Examiner* — Jessica Worsham
(74) *Attorney, Agent, or Firm* — Brooks Kushman P.C.

(57) ABSTRACT

Water-in-oil invert emulsions containing no surfactant are formed by simple mixing of water with organopolysiloxanes containing all of aralkyl, long chain alkyl, and hydrophilic groups. The surfactant-free water-in-oil invert emulsions have a wide variety of uses, for example in compositions for surface care, antifog coating compositions, cosmetic compositions, and hair care compositions.

12 Claims, No Drawings

SURFACTANT-FREE ORGANOPOLYSILOXANE INVERT EMULSIONS

BACKGROUND OF THE INVENTION

1. Field of the Invention

The present invention pertains to water-in-oil emulsions wherein the oil phase is a self-emulsifying organopolysiloxane. The water-in-oil emulsions can be prepared in the absence of emulsifying surfactants.

2. Description of the Related Art

Emulsions of organopolysiloxanes are known, and are of two major types. The first, and most common type, are oil-in-water ("O/W") emulsions. Such emulsions are produced by dispersing an organopolysiloxane ("silicone") into water with the aid of a surfactant or dispersing aid. A large number of different types of surfactants, or "emulsifiers" may be used, including anionic surfactants, cationic surfactants, zwitterionic surfactants, and non-ionic surfactants, particularly the latter. Partially hydrophobic inorganic particles in the nanometer size range may also be used, these particles containing both hydrophobic and hydrophilic portions which mimic conventional surfactant structure.

Less common are water-in-oil (W/O) emulsions. Preparation of such emulsions has been described in the literature as technically difficult, requiring different surfactants and surfactant concentrations as compared to O/W emulsions, and possessing different stability profiles. In the case of both types of emulsions, freedom from separation, i.e. storage stability, is a major concern.

A further problem with both types of emulsions is that a considerable surfactant quantity is necessary to produce small dispersed phase particle sizes and maintain stability. Unfortunately, in many applications, particularly in the personal care sector, e.g. cosmetics, body lotions, shampoos, etc., the choice of surfactant is limited due to potential irritation. Furthermore, many of the surfactants can leave the skin, for example, with a soapy or tacky feel.

Stable W/O emulsions have been described in the literature as difficult to make compared to O/W type because of their inherent instability. One of the most common reasons for their inherent instability is the absence of clearly defined electrical double layer surrounding the dispersed phase droplets, which would prevent the droplets from coalescence. In almost all examples previously reported, a surfactant or a solubilizer as well as high shear is essential to make a stable W/O emulsion.

Water-in-oil (W/O) emulsions, also called invert emulsions, are highly sought after for applications in personal care, surface care, pharmaceuticals and in the oil and gas industry. However, W/O type emulsions are more difficult to make compared to O/W type emulsions because of their inherent instability (Klein, K. Formulating Water-in-Oil Emulsions: A Scary Endeavor, Cosmetics & Toiletries, 24-25, (2006). See Also, makingcosmetics.com/articles/27-how-to-make-water-in-oil emulsions). To make a water-in-oil emulsion, an external surfactant or solubilizer is almost always necessary to make the oil phase and the aqueous phase blend with each other. U.S. Pat. Nos. 5,853,711 and 7,914,772 B2 describe W/O compositions for cosmetic application. U.S. patent application Ser. No. 11/699,906 describes the use of a silicone W/O emulsion composition for drug delivery. Patent application PCT/US2004/040603 describes a water-in-oil emulsion wax composition for cleaning and polishing. International patent application WO 2000069423 Al describes invert emulsions for cleaning skin or hard surface by application with a wipe. The use of external surfactants, which mostly are of low molecular weight, can sometimes negatively impact the properties of the composition. For example, in cosmetics many surfactants are of concern for their irritancy and allergic reactions on the skin. For paint formulation, leaching of surfactants has a detrimental effect on the appearance of the painted surface. Besides, the addition of emulsifiers adds complexities to the system and adds to processing steps and cost. Thus, it would be advantageous if W/O emulsions of silicones can be made without the addition of any external surfactants.

U.S. Pat. No. 5,643,555 describes emulsifier-free W/O emulsions for cosmetics applications, which were stabilized by polyalkylsilsesquioxanes. U.S. Pat. No. 6,379,680 B2 describes emulsifier-free W/O emulsions stabilized by finely dispersed, micronized inorganic pigments. Also, U.S. Pat. No. 6,391,321 B1 describes both o/w and w/o type emulsifier-free emulsions stabilized by microfine solid particles. These prior arts use the concept of "pickering emulsions" that need finely divided solid particles to stabilize the emulsions. Such stabilizing particles are also included within the definition of "surfactant" herein, as they function in the same manner, albeit being of substantially inorganic nature. Such "pickering" particles may also be termed "dispersants."

Water-in-oil emulsions have some unique advantages, including the ability to be formulated with additional non-polar ingredients. For example, fragrances and emollients such as lanolin can be added directly by simple mixing, which is not the case with O/W emulsions.

It should be desirable to provide invert emulsions, and particularly microemulsions, which possess the desirable attributes of such emulsions, which are stable, and which do not require the use of surfactants with their disadvantages.

SUMMARY

It has now been surprisingly and unexpectedly discovered that organopolysiloxanes which bear all of long chain alkyl groups, aralkyl groups, and a hydrophilic group can be mixed with an aqueous phase to form storage stable invert emulsions without the use of a surfactant. Stable water-in-oil emulsions consisting of 20% or more water as the internal (dispersed) phase and one or more self-emulsifying organopolysiloxanes as the outer (dispersing phase) can be prepared. The emulsions can be transparent, translucent or opaque in appearance and liquid, gel-like or creamy in consistency. The emulsions form without the addition of any external surfactant and preferably without the need for high shear mixing. Other additives such as thickeners, colorants, preservatives, etc. may be optionally added either to the aqueous phase or the oil phase to suit the particular area of application.

DETAILED DESCRIPTION

The self-emulsifying organopolysiloxanes are liquids at 25° C., and may be linear, lightly branched, or highly branched, and contain on average per molecule, at least one long chain alkyl group, at least one aralkyl ("arylalkyl") group, and at least one hydrophilic group, defined herein as an alkylene-bonded polyether group, alkylene-bonded polyhydroxyl compound, or alkylene bonded saccharide or derivative thereof. The hydrophilic groups are thus preferably non-ionic in nature.

More particularly, the branched organopolysiloxanes of the emulsions of the invention are essentially low molecular weight oligomers corresponding generally to the formula $$M_a T_b Q_c$$

where M, T, and Q units have their conventional meaning, for example as described by Walter Noll, Chemistry and Technology of Silicones, Academic Press, New York, pp. 2 to 7. In these organopolysiloxanes, all silicon atoms are tetravalent, preferably all silicon atoms are linked to another silicon atom or to other silicon atoms through siloxane

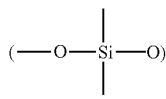

linkages, a is an integer of 3 or greater, b is 0-4, preferably 0 or 1, and c is 0-2, preferably 0 or 1, with the proviso that the sum of b and c is at least 1, and is preferably 1.

Thus, the M groups correspond to $R_e R^1_f R^2_g R^3_h SiO_{(4-(e+f+g+h))/2}$ where e, f, g, and h are all 0-3, and the sum of e, f, g, and h is 3. In these M groups, and also relevant to T groups, R is a lower $C_{1-7}$ alkyl group or an aryl group;
$R^1$ is an aralkyl group;
$R^2$ is an alkylene-bonded polyether group or an alkylene-bonded polyhydroxyl compound or alkylene-bonded saccharide or derivative thereof; and
$R^3$ is a long chain alkyl group having eight or more carbon atoms.

The T units correspond to the formula $R_{e'} R^1_{f'} R^2_{g'} R^3_{h'} SiO_{(4-(e'+f'+g'+h'))/2}$ where e', f', g', and h' are 0 or 1 and the sum of e', f', g', and h' is 1, where R, $R^1$, $R^2$, and $R^3$ have the same meanings as in the M units. In the $M_a T_b Q_c$ branched organopolysiloxanes, it is preferable that not more than one surfactant group be present.

The Q units correspond to the formula $SiO_{4/2}$.

R are preferably, and independently of each other, hydrocarbon groups directly bonded to silicon by Si—C bonds, which are readily available in the form of their hydrolysable silane organopolysiloxane precursors. As is well known, organopolysiloxanes are generally prepared by hydrolysis or cohydrolysis of chlorosilanes and/or alkoxysilanes. The most readily available and most inexpensive precursors contain methyl or phenyl groups as R. However, other silanes can be readily synthesized.

Thus, R may be, for example a lower $C_{1-7}$ alkyl group such as a methyl, ethyl, 1-propyl, 2-propyl, 1-butyl, or 2-butyl group. Hexyl and heptyl groups are also possible, but not preferred. These lower alkyl groups are also defined herein as including cyclopentyl and cyclohexyl groups, optionally methyl substituted. The aryl groups R are optionally substituted phenyl, napthyl, anthryl, and phenanthryl groups, preferred substituents being methyl and ethyl groups, when present. When R is an aryl group, it preferably contains 6 to 16 carbon atoms, more preferably 6 to 10 carbon atoms, and most preferably 6 carbon atoms, i.e. a phenyl residue. Most preferably, all R are methyl groups. R may also be a $C_{2-6}$ alkenyl group such as a vinyl group, but this is also not preferred.

$R^1$ is an aralkyl group. These groups may initially be present in a starting hydrolysable silane, or are preferably added later by hydrosilylation, as described later; the same is true for the $R^2$ and $R^3$ groups. Preferred $R^1$ groups are aralkyl groups where the alkyl group contains 2-6 carbon atoms, preferably 2-3 carbon atoms and most preferably 2 carbon atoms and the aryl group is an optionally substituted phenyl, napthyl, anthryl, or phenanthryl group, preferably a phenyl or naphthyl group, and most preferably a phenyl group. Among the substituents on the aryl group which are possible are preferably $C_{1-4}$ alkyl groups; halo groups such as chlorine; cyano groups; alkoxy groups, and the like. Preferably the aryl groups are unsubstituted or substituted with methyl or ethyl groups, preferably methyl groups. Cyano and chloro substitution is also preferred, as these increase the refractive index. An aralkyl precursor is an arylalkenyl compound. Examples include styrene and α-methylstyrene, which are preferred, and m-cyanostyrene, o-cyanostyrene, and various dichlorostyrenes.

$R^2$ is an aliphatically bound hydrophilic group, preferably an alkylene-bonded polyoxyalkylene polyether group. As a precursor, an alkenol such as allyl alcohol can be oxyalkylated with one or more alkylene oxides in the conventional manner, for example oxyalkylation with a basic catalyst or a double metal cyanide catalyst. The alkylene oxides used include ethylene oxide, propylene oxide, and butylene oxide, although other alkylene oxides are possible, especially when used in minor proportions. Since the polyoxyalkylene polyether moiety is responsible in the largest part for the hydrophilicity and dispersibility of the inventive organopolysiloxanes, it is preferable that the polyether moieties contain predominantly oxyethylene units, i.e. greater than 50 mole percent oxyethylene units. As a second unit to be used in such polyethers, oxypropylene units are most preferred. As the amount of $C_3$ or higher oxyalkylene units increases, the hydrophilicity decreases. Polyethers which contain a majority of oxyethylene units, for example greater than 70 mole percent, more preferably greater than 80 mole percent, yet more preferably greater than 90 mole percent, and most preferably 100% of oxyethylene units, are preferred. The non-alkenyl terminus of the polyether may be a free hydroxyl group, or it may be capped, for example, but not by limitation, with an alkyl ether or ester group.

As a result of using such precursors in the synthesis of the inventive organopolysiloxanes, $R^2$ generally is of the formula $$—R^5—(OA)_n-OR^6$$

wherein $R^5$ is a $C_{2-20}$ alkylene group, preferably an ethylene group or a propylene group, A is a $C_{2-4}$ alkylene group, which may be the same or different in the n repeating (OA) units, preferably a $C_{2-3}$ alkylene group, and most preferably an ethylene group, an n is an integer which is from 4 to 100, preferably 6-50, and more preferably 8-20. The n (OA) units, when A is different in different (OA) units, may be present in block from, random form, or combinations of these.

$R^6$ is hydrogen, alkyl, for example $C_{1-18}$ alkyl, or

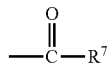

where $R^7$ is $C_{1-18}$ alkyl.

$R^2$ may also be an alkenyl-substituted polyhydroxy compound or saccharide (including polysaccharides). Polyhydroxy compounds are compounds such as polyglycerol, which contain numerous hydrophilic hydroxyl groups. Such numerous hydroxyl groups are also contained in mono- and polysaccharides such as glucose, fructose, mannose, sucrose, low molecular weight celluloses and modified celluloses, e.g. methyl cellulose, carboxymethyl cellulose, and the like. Alkenyl groups can be attached by conventional methods, such as etherification with an unsaturated alcohol such as allyl alcohol, or by esterification with an unsaturated carboxylic acid, carboxylic acid anhydride, or carboxylic acid chloride, examples being (meth)acrylic acid, (meth)acryloyl chloride, and (meth)acrylic anhydride. One process for producing unsaturated saccharides is disclosed in WO 2012/013648, while an enzymatic synthesis from unsaturated alcohol and saccharide or polysaccharide using glycosidase as a catalyst is disclosed in U.S. published application 2012/0028308 A1.

The long chain alkyl group $R^3$ is a $C_{8-40}$ alkyl group, more preferably a $C_{8-20}$ alkyl group, and most preferably a $C_{10-18}$ alkyl group. Longer chain alkyl groups may confer greater oil compatibility, but may not be as readily available. The precursor to the long chain alkyl groups are the corresponding monounsaturated alkenes, preferably an α-olefin. For example, a dodecyl group precursor would be 1-dodecene. Most preferably, the long chain alkyl group contains 14 or more carbon atoms.

Most preferably, the branched organopolysiloxanes in the emulsions of the present invention are branched $Si_4$ or $Si_5$ molecules of the formulae:

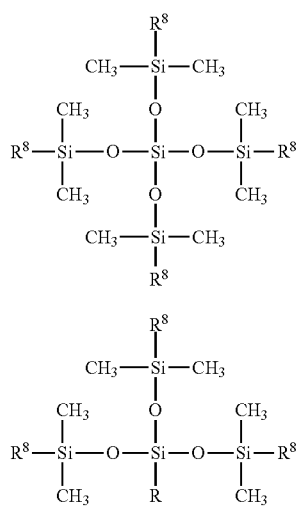

where R is preferably phenyl, and wherein each $R^8$ individually is $R^1$, $R^2$, or $R^3$, with the proviso that on average, one of each of $R^1$, $R^2$, and $R^3$ is present per molecule.

A significant advantage of the branched self-emulsifying organopolysiloxanes useful in the emulsions of the subject invention is that they are substantially free of cyclic siloxanes, for example D4 (octamethylcyclotetrasiloxane) and D5 (decamethylcyclopentasiloxane). This is accomplished due to the method of preparation of the branched organopolysiloxanes, in which the various $R^1$, $R^2$, and $R^3$ groups are preferably bonded through hydrosilylation. Also, since the linkages between $R^1$, $R^2$, and $R^3$ are by Si—C bonds, rather than Si—O—C bonds, the organopolysiloxanes are stable to hydrolysis.

In a preferred method of synthesis, a branched organopolysiloxane with Si—H functionality is provided. The number of Si—H groups is preferably the same as the number of $R^1$, $R^2$, and $R^3$ groups to be attached. These starting materials are commercially available or are able to be synthesized by methods conventional in organosilicon chemistry.

For example, the Si—H functional starting materials may be formed by cohydrolysis of the respective Si—H functional silanes. For preparation of an Si—H functional starting material of formula

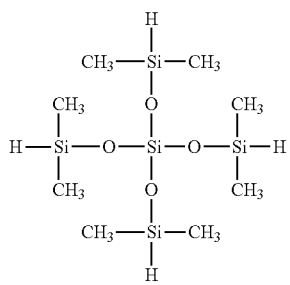 [SMILES: C[SiH](C)O[Si](O[SiH](C)C)(O[SiH](C)C)O[SiH](C)C]

for example, four or more moles of dimethylchlorosilane may be condensed in aqueous medium, preferably aqueous alcoholic medium, with one mole of tetrachlorosilane, off-gassing HCl. Unreacted dimethylchlorosilane may be removed by distillation from a resulting non-aqueous phase containing the branched product.

The Si—H functional starting compound is then reacted with the ethylenically unsaturated $R^1$, $R^2$, and $R^3$ precursors in a noble metal catalyzed hydrosilylation reaction. The hydrosilylation catalyst may be any useful hydrosilylation catalyst. Most hydrosilylation catalysts are noble metals, or compounds or complexes of noble metals, e.g., rhodium, iridium, palladium or platinum, but platinum compounds are generally preferred due to their generally higher activity. For example, as hydrosilylation catalysts it is possible to use metals and their compounds, such as platinum, rhodium, palladium, ruthenium, and iridium, preferably platinum and rhodium. The metals may optionally be fixed to finely divided support materials, such as activated carbon, or metal oxides such as aluminum oxide or silicon dioxide. Preference is given to using platinum and platinum compounds. Particular preference is given to those platinum compounds which are soluble in polyorganosiloxanes. Soluble platinum compounds that can be used include, for example, the platinum-olefin complexes of the formulae $(PtCl_2.olefin)_2$ and $H(PtCl_3.olefin)$, preference being given in this context to the use of alkenes having 2 to 8 carbon atoms, such as ethylene, propylene, isomers of butene and of octene, or cycloalkenes having 5 to 7 carbon atoms, such as cyclopentene, cyclohexene, and cycloheptene. Other soluble platinum catalysts are the reaction products of hexachloroplatinic acid with alcohols, ethers, and aldehydes or mixtures thereof, or the reaction product of hexachloroplatinic acid with methylvinylcyclotetrasiloxane in the presence of sodium bicarbonate in ethanolic solution. Platinum catalysts with phosphorus, sulfur, and amine ligands can be used as well, e.g., $(Ph_3P)_2PtCl_2$. Particularly preferred are complexes of platinum with vinylsiloxanes, such as sym-divinyltetramethyldisiloxane. Other hydrosilylation catalysts are known from the patent and non-patent literature.

The branched silicones of the subject invention are prepared through hydrosilylation of the $R^1$, $R^2$, and $R^3$ precursors, these precursors containing a hydrosilylatable carbon-carbon multiple bond. The hydrosilylation may be concerted, pseudoconcerted, or completely stepwise relative to the addition of reactants, but is preferably stepwise. The order of hydrosilylation is not critical, but it is preferred that the arylalkene be reacted first, followed by the alkene, and finally by the alkenyl-functional hydrophilic species. It has been found that when the alkene is reacted last, that significant isomerization may occur, requiring a higher amount of alkene. Excess or unreacted $R^1$, $R^2$, or $R^3$ precursors may be removed by conventional methods, i.e. by distillation. While it is highly preferable that all unreacted $R^1$ precursors be removed, it may be advantageous for economical reasons to leave in unreacted $R^2$ precursor, which may perform the function of an emulsifier, or to leave in unreacted $R^3$ precursor, which may serve as an oily diluent.

The preferred synthetic routes to the inventive organopolysiloxanes involve hydrosilylation, but the preceding description is not limiting. For example, instead of one or more M units containing Si—H functionality, a hydrolzable M unit containing one of $R^1$, $R^2$, or $R^3$ already bound to silicon may be used during preparation of the branched Si—H functional organopolysiloxane starting material, with the remaining $R^1$, $R^2$, or $R^3$ groups added by hydrosilylation as described above.

Thus, the preferred starting materials correspond to the formula

$M_iT_jQ_k$ where i, j and k correspond, respectfully, to the values a, b, and c of the inventive organopolysiloxanes, M contains at least one silicon-bonded hydrogen atom, and preferably is of the formula $(CH_3)_2Si(H)O_{1/2}$, T is of the formula $HSiO_{3/2}$ or $BSiO_{3/2}$ where B is selected from among R, $R^1$, $R^2$, or $R^3$, and Q is $SiO_{4/2}$.

While it is possible that the substituents of the M groups of the inventive organopolysiloxanes might contain two or more $R^1$, $R^2$, or $R^3$ groups, for example by employing a starting material having M groups such as $H_3SiO_{1/2}$, or $H_2(CH_3)SiO_{1/2}$, this is not preferable. It is most preferable that the M groups individually contain but one of $R^1$, $R^2$, and $R^3$. In this case, the necessary $R^1$, $R^2$, and $R^3$ groups will be distributed among 3 or 4 or more M groups in the molecule, or among the M groups and T groups.

It is unavoidable that there will also be a proportion of organopolysiloxanes present in the product mixture which do not contain all of $R^1$, $R^2$, and $R^3$ groups. However, generally, in order of increasing preference, 50, 60, 70, and 80 mole percent or more of the molecules will contain all three of $R^1$, $R^2$, and $R^3$. It appears that a stepwise synthesis involving initial hydrosilylation of an arylalkene, followed stepwise by the long chain alkene, and finally hydrosilylation of the alkenyl-terminated polyether, results in a high proportion of product whose molecules contain all of the $R^1$, $R^2$, and $R^3$ groups. The statistical "dilution" of the desired product with organopolysiloxanes containing predominantly only two of $R^2$ and $R^3$ does not impair the usefulness of the product, in forming invert emulsions.

An advantage of both the lower molecular weight, branched organopolysiloxanes just described, as well as the linear or lightly branched organopolysiloxanes to be described later, is that they possess high refractive indexes, which is important in many applications. The refractive index is generally greater than 1.45, preferably greater than 1.46, and most preferably greater than 1.47. By way of comparison, a conventional polydimethylsiloxane fluid of 100 mPa·s viscosity has a refractive index of about 1.4, while a similar, phenyl substituted fluid has a refractive index of about 1.46.

The linear or lightly branched self-emulsifying organopolysiloxanes contain aralkylsiloxy moieties, siloxy moieties bearing at least one long chain alkyl group, siloxy moieties bearing a hydrophilic group, optionally lower dialkylsiloxy moieties, and are preferably prepared by hydrosilylation, rather than cohydrolysis or equilibration. Thus, they contain no objectionable quantity of cyclic organopolysiloxanes. However, other methods of preparation are suitable as well, particularly when cyclic siloxanes are tolerable or desired.

The linear or lightly branched, self-emulsifying organopolysiloxanes generally correspond to the structural formula (I):

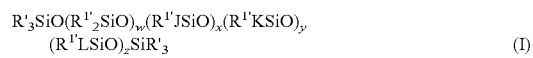

$$R'_3SiO(R^{1'}_2SiO)_w(R^{1'}JSiO)_x(R^{1'}KSiO)_y(R^{1'}LSiO)_zSiR'_3 \qquad (I)$$

wherein each R', independently of each other, is a $C_{1-30}$ hydrocarbon group, preferably an alkyl, cycloalkyl, aryl, aralkyl, or alkaryl group having 1 to 30 carbon atoms, and in the case of R' containing aryl groups, containing at least 5 ring atoms, in addition to which the aryl rings of the aryl, alkaryl, or aralkyl group may also contain heteroatoms selected from the group of oxygen, sulfur, nitrogen, and phosphorus, or R' may be another organic group or inorganic group which is substantially unreactive in hydrosilylation reactions or will not inhibit hydrosilylation, for example a hydroxyl group, acyloxy group, or alkoxy group, the alcohol moiety of the alkoxy group containing preferably from 1 to 4 carbon atoms, most preferably a methoxy or ethoxy group, or R' is an L group. R' is preferably a $C_{1-6}$ alkyl group, phenyl, phenylethyl, 2-phenylpropyl, or naphthylethyl group, and most preferably for reasons of economy, a methyl group.

$R^{1'}$ each independently may be a $C_{1-30}$ hydrocarbon group, preferably an alkyl group, a cycloalkyl group, aryl group, aralkyl group, or alkaryl group, wherein the aryl groups may contain heteroatoms as for R', more preferably a $C_{1-4}$ alkyl group, a phenyl group, or oxyalkyl group and most preferably a methyl group. $R^{1'}$ may also be hydrogen, as a result of excess Si—H bound hydrogen in the H-siloxane reactant, or as a result of incomplete reaction.

The group J is an aralkyl moiety which is preferably the residue of a compound able to be attached to the organopolysiloxane backbone by a hydrosilylation reaction. J is preferably phenylethyl, 2-phenylpropyl, 3-phenylbutyl, or naphthylethyl. Most preferably, J is 2-phenylpropyl. It is preferred that the $R^{1'}$ moiety in the $R^{1'}JSiO$ siloxy units is methyl or phenyl, and the $R^{1'}JSiO$ siloxy units are preferably substituted such that the starting organohydrogen-polysiloxane does not need to contain any substantial quantities of $H_2SiO$ groups, or siloxy groups bearing both Si—H bound hydrogen and an organic group other than methyl or phenyl, which would increase expense. In the preferred polymers, in the $R^{1'}JSiO$ siloxy groups, R' is phenyl or $C_{1-4}$ alkyl, preferably methyl. Groups J preferably have 8-30 carbon atoms, more preferably 9-13 carbon atoms.

K is a long chain alkyl group having at least 8 carbon atoms, and preferably not more than 45 carbon atoms, more preferably not more than 30 carbon atoms. K is preferably a $C_8$ to $C_{20}$ alkyl group, more preferably a $C_8$ to $C_{18}$ alkyl group. The K groups are derived from hydrosilylation of the appropriate alkene, such as 1-octene, 1-dodecene, 1-octadecene, etc. As with the $R^{1'}JSiO$ siloxy units, in the $R^{1'}KSiO$ siloxy units, it is preferred that R' is methyl or phenyl.

The group L is a hydrophilic species, which, in conjunction with the hydrophobic species J, K, and when present, R or $R^1$ species which are aryl, cycloalkyl, aralkyl, or alkaryl, aid in conferring self-emulsifying properties, in particular ready self-emulsifying properties when used as the external phase in invert emulsions. In these silicones L may be independently selected from Si—C-bonded polyoxyalkylene polyethers having the formula (II)

$$—R^5—(OA)_n-OR^6 \qquad (II)$$

as described previously. The group L may also be a polyhydroxy compound of the formula $$—R^a—O\text{-(glyceryl or polyglyceryl)} \qquad (III)$$

a saccharidyl group of the formula —$R^a$—O-(monosaccharide or polysaccharide) (IV); or a polyvinylalcohol homopolymer or copolymer of the formula —$R^a$-(polyvinylalcohol homo or copolymer) (V). These groups may also be used as $R^2$ groups as previously described for the branched, self-emulsifying organopolysiloxanes.

The groups L thus are, independently of one another, hydrophilic species which contain a plurality of hydroxyl groups or are polyether groups, or mixtures thereof. L are bonded through an alkylene or alkylenyl group derived from hydrosilylation of an alkenyl or alkynyl group bonded to the hydrophilic moiety of the L group, and are preferably selected from polyoxyalkylene polyethers terminated on one end with a hydrosilylatable group, preferably a vinyl or allyl group, and terminated on the other end by alkyl, aryl, alkaryl, aralkyl, hydroxyl, alkoxy, carboxy, or other groups such as sulfate ester, phosphate ester, or other terminating groups which do not interfere with a hydrosilylation reaction. L may also contain a glyceryl or polyglyceryl species, a monosaccaridyl or polysaccharidyl species or polyvinylalcohol species, for example. The groups L are groups derived from hydrosilylation of an unsaturated compound containing the hydrophilic moiety.

For example, and by preference, the L group may be an alkylpolyether moiety —$R^9$—O(CH$_2$CH$_2$)$_p$—(C$_3$H$_6$O)$_q$(C$_n$H$_{n+2}$O)$_r$—$R^b$ wherein $R^9$ is a C$_2$-C$_{20}$ divalent hydrocarbon group, n is 4-10, and $R^b$ is preferably a C$_{1-20}$ hydrocarbon, more preferably an alkyl, cycloalkyl, aryl, aralkyl, or alkaryl group or a hydroxyl or acyl group, and most preferably a hydroxyl, methyl, butyl, or acetyl group. To be hydrophilic, the p and q groups must dominate, preferably the p groups. The variables p and q have values in the range of 0-30, preferably 0-20 but at least one p, q, or r group must be present. Most preferably, r is less than 4 and preferably 0, q is less than or equal to about 20 (on average). The sum of p+q+r must be about 6 or higher, and the molecular weight of L preferably ranges from about 300 to about 6000. The p, q, and r units may be present randomly distributed, as homopolymeric blocks, as heteric blocks, or in any desired distribution. If homopolymeric oxypropylene or oxy(higher alkylene) blocks are employed, such blocks cannot be so long as to confer hydrophobicity rather than hydrophilicity or a combination of hydrophilicity and oleophilicity. For example, it is relatively well known that polyoxypropylene homopolymer polyethers with molecular weights above 400-500 Daltons are oily and hydrophobic, whereas low molecular weight analogues such as propylene glycol, dipropylene glycol, and tripropylene glycol are quite hydrophilic. In the case of higher polyoxyalkylenes such as polybutylene glycol, e.g., polytetramethylene glycol, the higher carbon to oxygen ratio renders such oligoethers and polyethers hydrophobic at yet lower molecular weights. Thus, homopolyoxyethylene glycol and copoly(oxyethylene/oxypropylene)glycols, copoly(oxyethylene/oxybutylene)glycols, or terpoly(oxyethylene/oxy-propylene/oxybutylene)glycols are preferred. Again, it is the ready self-emulsifying properties of the product which is of paramount importance. This dispersibility is easily assessed, as indicated subsequently. The use of block copolyethers or block/heteric copolyethers derived from ethylene oxide and propylene oxide may be particularly useful.

L may also contain a glyceryl or other highly hydroxyl group-containing species such as a derivative of pentaerythritol, polyglycerine, a saccharide or polysaccharide, or the like. Glycosyl species are particularly preferred. Species such as glycerine, polyglycols, polyglycerols, oligo and polysaccharides, and polyvinyl alcohol, all hydrophilic species, may be derivatized by conventional techniques in organic chemistry to generate a derivative having at least one and preferably substantially only one ethylenically (or ethylynically) unsaturated, hydrosilylatable group. Thus, for example, vinyl groups, allyl groups, acrylato or methacrylato groups may be present in these derivatives. In the case of the polyethers, the polyethers may be synthesized by oxyalkylation of allyl alcohol or another unsaturated alcohol. In the case of hydroxyl-functional hydrophilic groups such as glyceryl, polyglyceryl, saccharidyl, or polyvinyl alcohol, the base substances can be etherified or esterified with unsaturated groups, or reacted with unsaturated isocyanates or the like, to introduce the necessary ethylenic or ethylynic unsaturation.

The polyvinylalcohol hydrophilic moieties may be homopolymeric or copolymeric. Polyvinylalcohols are generally prepared by hydrolysis of polyvinyl esters, predominately polyvinyl acetate, polyvinylpropionate, and mixed polyvinyl(acetate/propionate). The hydrolysis may be substantially complete, i.e. from 95-99 mol percent or more complete, or may be partial. The greater the content of remaining ester groups, the less hydrophilic is the resulting polymer. The polyvinyl alcohols, whether completely hydrolyzed or not, may also be modified, for example by acetalization with aldehydes such as formaldehyde, acetaldehyde, propionaldehyde, or butyraldehyde. The higher the degree of acetalization, the less hydrophilic the copolymer. In addition, copolymer polyvinyl alcohols may be prepared by hydrolyzing a mixed polyvinyl ester polymer such as a copolymer of ethylene and vinyl acetate. The more ethylene units are present, the less hydrophilic is the copolymer following hydrolysis. Other monomers which result in groups which do not interfere with a hydrosilylation reaction may also be present. Whether a particular group interferes with hydrosilylation can be routinely determined by hydrosilylating the copolymer, bearing an unsaturated carbon-carbon bond as described previously, in a test hydrosilylation of this one component with an Si—H functional organopolysiloxane. By choice of appropriate comonomers, derivatization (such as by acetalization), and by adjusting the degree of hydrolysis of vinyl ester groups, a wide range of hydrophilicity can be obtained.

The amphiphilic silicones of the invention may also contain chain extending groups and crosslinking or branching groups containing a silicon-carbon bonded hydrocarbon radical or hydrophilic group. The chain extending groups may be prepared, for example, by reaction of an H-siloxane containing SiH-functional terminal groups with a compound bearing two hydrosilylatable unsaturated groups. Examples of such compounds are divinylbenzene, α,ω-dienes, and α,ω-allyl-terminated polyoxyalkylene polyethers. Essentially, these bis-unsaturated groups correspond to the R, $R^1$, J, K, and L groups discussed previously, but containing at least two sites of carbon-carbon unsaturation.

Thus, the preferred chain extending groups correspond to those of the formula $$[O_{1/2}R^1{}_2Si—R^*—SiR^1{}_2O_{1/2}]_t \qquad (VI)$$

where t is 0-100, preferably 0-50, more preferably 0-20, yet more preferably 0-5, and most preferably 0-3. Preferably, no chain extending groups are present, except as unavoidable linkages formed from impurities in the reactive components. R* is a hydrocarbon radical having 4-30 carbon atoms SiC bonded to both silicon atoms of the chain extending group, or a hydrophilic group SiC bonded to both silicon atoms through a $C_{2-20}$ hydrocarbon linkage, preferably a $C_{2-4}$ hydrocarbon linkage. The R* units may also be defined as J', K', and L' groups, as may also be the R* groups of branching structures described above, these J', K', and L' groups corresponding to the definitions of the J, K, and L groups, but carrying an additional site of hydrosilylatable unsaturation.

The branching or crosslinking groups preferably are those of the formula

 (VII)

where u is 0-100, preferably 0-50, more preferably 0-20, yet more preferably 0-5, and most preferably 0-3. In the branching groups, R" is a divalent branching moiety which links the branching unit via R" with at least one other siloxy group so as to form a branch in the organopolysiloxane at this point. The at least one other siloxy group may be the terminus of an organopolysiloxane chain, or may be a siloxy group within an organopolysiloxane chain. Thus, dendrimer and ladder like branched and crosslinked polymers may be formed.

The chain extension may be used to control the molecular weight, but it is difficult to do so without also increasing the amount of branching and crosslinking. The larger the amount of chain extension, the higher the molecular weight and viscosity. Increasing branching also in general leads to higher viscosities. Thus, both chain extension and branching/crosslinking can be used to tailor polymer properties.

The bis-hydrosilylatable compounds which ultimately form the R* and R" groups of the chain extending and branching/crosslinking groups can be added at any time during preparation of the amphiphilic silicones of the invention. Unless added in very small amounts, however, it is desirable that they be added toward the end of the synthesis, since branching and crosslinking may interfere with the ease of hydrosilylation or may cause solubility problems. The R* group precursors may be added both at the beginning and toward the end of the reaction. When branching groups or chain extending groups are present, it is preferred that the R" groups be derived from bis(alkenyl or alkynyl) hydrophilic moieties. One such preferred moiety is an α,ω-bis(allyl) terminated polyoxyalkylene polyether, as described earlier for the L groups of the amphiphilic silicone.

The preparation of such hydrosilylatable derivatives containing hydrophilic groups and hydrosilyatable carbon-carbon multiple unsaturation is known from conventional organic chemistry and well known to those skilled in the art. Preferably, L is an oxygen-containing, Si—C bonded hydrophilic group having a molecular weight of 100 Daltons or more. In a preferred embodiment, the self-emulsifying silicones are those which are preparable by reacting hydrosilylatable compounds which will supply the groups J, K, and L, with a polysiloxane whose internal repeating units are substantially dimethylsiloxy, methylhydrogensiloxy, and optionally but not preferably, dihydrogensiloxy units. The H-siloxane may or may not contain Si—H bound hydrogen in its terminal units as well. Polysiloxanes containing methylphenylsiloxy, diphenylsiloxy, and phenylhydrogen siloxy groups in addition or in lieu of to the groups just mentioned are also preferred. The terminal groups are preferably trimethylsilyl groups, but any suitable terminal group which does not interfere with hydrosilation may be used, for example dimethylphenylsiloxy, hydrogendimethylsiloxy, hydroxyldimethylsiloxy, etc. Such Si—H-containing siloxanes, sometimes termed "H-siloxanes" are readily available commercially, or can be synthesized by methods well known in organosilicon chemistry. For reasons or economy, the H-siloxanes are preferably poly(methylhydrogensiloxy/dimethylsiloxy) silicones with trimethylsilyl termination, for example those of the formula

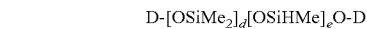

where D independently is HMe$_2$Si or Me$_3$Si, and
where e is preferably equal to the sum of x, y, and z, and the sum of d and e is such that the desired molecular weight and/or chain length is obtained. In other words, preferably substantially all of the groups J, K. and L are bonded to the amphiphilic silicone by hydrosilylation with the H-siloxane. However, it is also possible that the H-siloxane may contain some of the groups J, K. and L already as R$^1$ groups, i.e. prior to hydrosilylation. For reasons of economy, this is not preferable.

The amphiphilic silicones of the subject invention are prepared through hydrosilylation of J, K. and L precursors, as discussed in U.S. Pat. No. 8,524,262, which is incorporated herein by reference.

The inventive invert emulsions are prepared by mixing the organopolysiloxanes with water. In view of the admonitions of the prior art, the ease with which the invert emulsions are formed is highly surprising and unexpected. Prior preparations have required surfactants, solubilizers, or dispersants, and generally required high shear mixing as well.

The self-emulsifying organopolysiloxanes may be combined with numerous additional components, either prior to emulsifying into the invert emulsion, or afterwards. Some of the additional components are, for example, thickeners which increase the viscosity of the external (oil) phase; diluents which decrease the viscosity of the external phase; natural and synthetic oils; organic solvents; waxes, both liquid and solid; fragrances; biocides; pharmaceutical active ingredients; emollients; humectants; organopolysiloxanes other than the self-emulsifying organopolysiloxanes, such as polydimethylsiloxanes (dimethicones), silicone resins, volatile silicones such as octamethylcyclotetrasiloxane (D4) and decamethylcyclopentasiloxane (D5); abrasive particles such as micro- and nano-size alumina, silica, titania, and ceria; fillers such as finely ground chalk, limestone, etc.; pigments, for example organic pigments and inorganic pigments such as the varied iron oxide pigments available in such colors such as yellow, brown, rust, red, and black, as well as other pigments conventionally used in the cosmetic arts, for example in lip stick, lip gloss, face creams, foundation creams, blushes, and mascara, etc.

The aqueous internal phase contains water, but may also contain other ingredients as well. These include, but are not limited to polar organic solvents such as lower alkanols, glycols, ketones, and esters. These should be soluble in the aqueous phase in the quantities used. Additional ingredients include water soluble fragrances; biocides; pharmaceuticals;

fine inorganic particles such as fumed or colloidal silica, alumina, titania, zinc oxide, and the like; thickeners which increase the viscosity of the aqueous phase, for example polyoxyalkylene polyethers containing polymerized higher alkylene oxides, polyacrylic acid, polymethacrylic acid, vegetable gums, starches, modified celluloses such as carboxymethylcellulose, hydroxypropylcellulose, etc.

In the case where additional components are added to either the external or internal phase, these components, in the amounts used, must not impair the ability to form a stable invert emulsion. Since the process for preparing the invert emulsions is very simple, only routine testing is required. Stability may be assessed by one of the methods discussed herein. In general, an invert emulsion can be assessed as stable if there is no visible separation into distinct phases after storage for one month at room temperature.

Based only on the weights of the self-emulsifying organopolysiloxanes and water, the invert emulsions contain 5 to 95 parts self-emulsifying organopolysiloxanes, preferably 10 to 90 parts, and more preferably, from 10 to 80, 10 to 70, 10 to 60, 10 to 50, 10 to 40, or 10 to 30 parts self-emulsifying organopolysiloxanes, balance water. One or a plurality of self-emulsifying organopolysiloxanes may be used. It is quite unusual that stable invert emulsions containing as much as 90% water may be prepared.

Surfactants are preferably wholly absent. However, it would not depart from the spirit of the invention to include a most minor amount of surfactant, i.e. to be "substantially free of surfactant" for example less than 0.5 weight percent based on the total weight of the invert emulsion, preferably, in order of increasing preference, less than 0.4%, 0.3%, 0.2%, 0.1%, 0.05%, and 0.01% by weight. Most preferably, no surfactant is present at all, i.e. the surfactant concentration is 0%. No surfactant is necessary to prepare the stable invert emulsions of the invention, and if a stable invert emulsion is formed without the aid of a surfactant, then the addition of surfactant, which does not alter the basic properties of the emulsion, e.g. stability, is within the scope of the invention, unless specified to the contrary.

Water-in-oil (W/O) emulsions, also known as invert emulsions, have oil phase as the external phase, which impart them a different set of benefits compared to the oil-in-water (O/W) types. For example, W/O emulsions are not water dilutable or water washable, have better barrier properties on substrates they are applied on and are less prone to bacterial contamination. Water-in-oil silicone emulsions find many applications including sun screens, facial make up, moisturizers, color cosmetics, pharmaceuticals, weed control composition and oil field drilling fluid systems.

These W/O silicone emulsions have good feel and spreadability and thus can be useful in cosmetics. Also, they are not water washable and thus can be used as antifog additives, steel polish and other surface care applications. Examples are provided.

The inventive invert emulsions are also free of solubilizers. Solubilizers are defined as organic liquids which are not surfactants, in whose absence a stable invert emulsion cannot be formed.

In the current invention, the finding that amphiphilic silicone molecules with aralkyl, alkyl and polyether functionalities attached to them easily form stable W/O emulsion without the aid of any external surfactant or solubilizer is unexpected and unique. The non-requirement of external surfactant or solubilizer gives definite advantages over conventional W/O emulsions formed with the help of external surfactants such as reduction in processing time, steps and cost.

Water-in-oil emulsions have a different set of benefits compared to the O/W types. For example, they are not water miscible, not water washable, impart better barrier properties on a substrate and are less prone to bacterial contamination. These properties make them suitable for additional application areas, such as cosmetics, surface care and antifog. Some of the water-in-oil emulsions are shear thinning, which property helps during their application on skin or another surface.

Preferably, stable water-in-oil emulsion consist of 20% or more water as the internal (dispersed) phase and one or more combination of the foregoing self-emulsifying organopolysiloxanes as the outer (dispersing phase). The emulsions can be transparent, translucent or opaque in appearance and liquid, gel like or creamy in consistency. The emulsions should form without the addition of any external surfactant and preferably without the need for a high shear. Other additives such as thickeners, colorants, preservatives, etc. may be optionally added either to the aqueous phase or the oil phase to suit the particular area of application.

Having generally described this invention, a further understanding can be obtained by reference to certain specific examples which are provided herein for purposes of illustration only and are not intended to be limiting unless otherwise specified.

EXAMPLES

General Conditions for the preparation of self-emulsifying organopolysiloxanes: a 4-necked round-bottomed flask, equipped with various neck adapters and stopcock-equipped bypass adapter to accommodate a mechanical stirrer, thermocouple, addition funnel, water condenser, nitrogen gas inlet and outlet, and rubber septum was used for hydrosilation. A heating mantle was used for heating the flask. An electronic thermostat was used in conjunction with the thermocouple to control heating of the flask and contents. The preparation was conducted under a mild flow of dry nitrogen gas. Upon completion of reaction, the water condenser was by-passed or removed and any volatiles were removed under vacuum. The product was cooled to below 40° C. and filtered under air or nitrogen pressure using a 0.45-10 μm nylon or polyester membrane filter with or without a pre-filter. The reactions are highly exothermic and must be controlled by adjusting the temperature and/or reagent addition rate.

Example 1

Preparation of a Linear Self-Emulsifying Organopolysiloxane

The reaction flask was charged with a poly(methylsiloxane-co-dimethylsiloxane) of approximate formula $M^H(D)_x(D^H)_yM^H$ [225.0 g, 0.786% w/w H content; x=7 approx., y=7 approx.]. The flask was heated to 80° C., alpha-methylstyrene (AMS, 160.7 g) was charged to the addition funnel, and approximately one-third of the AMS was added to the flask. The temperature of the flask contents was raised to about 100° C., and a solution of chloroplatinic acid in cyclohexanol (1% Pt w/w in the alcohol, 108 μL) was added quickly to the stirring (200-255 rpm) mixture in the flask via a syringe. A rapid exotherm ensued. AMS addition from the funnel was continued to keep the temperature in the range 140-160° C. from the heat of reaction. Upon completion of AMS addition, the mixture was heated at 145° C. for 30 minutes. The temperature was then lowered to 140° C., and 1-octadecene (51.5 g) was added slowly from the addition funnel. Immediately after the start of octadecene addition, an aliquot of Pt catalyst (108 µL) was added. After the octadecene addition had been complete, the mixture was heated for 30 minutes at 145° C. The temperature was set to 150° C., and poly(ethyleneoxide)monoallyl ether [10 mol EO, 106.8 g] addition was started at a rate of 3-4 mL/min. A further aliquot of catalyst (108 µL) was added following the start of polyether addition. The temperature was raised to 155° C. halfway through the polyether addition. The addition was completed without allowing the temperature to drop below about 150° C. The mixture was heated for one hour. Then, another aliquot of catalyst (108 µL) was added, and the mixture was heated for an additional hour. The reaction mixture was then stripped under vacuum (5-15 mm Hg) at about 170-180° C. to remove any residual volatile olefin. The off-white to straw-yellow product was then filtered after cooling to yield a slight hazy yellowish liquid. $^1$H NMR analysis showed the expected product. Viscosity—304 mPa·s. Refractive Index—1.478.

Example 2

Preparation of a Branched Self-Emulsifying Organopolysiloxane

The reaction flask was charged with tetrakis(dimethylsiloxy)silane [TDSS, 41.0 g, 1.225% w/w H content]. The flask was heated to 80° C. Alpha-methylstyrene (AMS, 29.4 g) was charged to the addition funnel, and approximately one-third of the AMS was added to the flask. The temperature of the flask contents was raised to about 100° C., and a solution of chloroplatinic acid in cyclohexanol (1% Pt w/w in the alcohol, 31 µL) was added quickly to the stirring (200-255 rpm) mixture in the flask via a syringe. A rapid exotherm ensued. AMS addition from the funnel was continued to keep the temperature in the range 140-160° C. from the heat of reaction. Upon completion of AMS addition, the mixture was heated at 145° C. for 30 minutes. The temperature was then lowered to 140° C., and 1-octadecene (33.0 g) was added slowly from the addition funnel. Immediately after the start of octadecene addition, an aliquot of Pt catalyst (15 µL) was added. After the octadecene addition had been complete, the mixture was heated for 30 minutes at 145° C. The temperature was set to 150° C., and polyoxyethylene monoallyl ether [10 mol EO, 63.0 g] addition was started at a rate of 3-4 mL/min. A further aliquot of catalyst (31 µL) was added following the start of polyether addition. The temperature was raised to 155° C. halfway through the polyether addition. The addition was completed without allowing the temperature to drop below about 150° C. At the end of the polyether addition, the temperature was raised to 155° C. The mixture was heated for one hour. Then, another aliquot of catalyst (31 µL) was added, and the mixture was heated for an additional hour. The temperature was maintained preferably in the range 155-160° C. throughout the total 2 hour mixing period since the completion of polyether addition. The reaction mixture was then stripped under vacuum (5-15 mm Hg) at about 160-180° C. to remove any residual volatile olefin. The off-white to straw-yellow product was then filtered after cooling to 40° C. to yield a clear, pale yellowish liquid. $^1$H NMR analysis showed the expected product. Viscosity: 157 mPa·s. Refractive Index: 1.4730.

Example 3

In a 250 mL plastic beaker, 30 g of the silicone fluid of Example 1, with octadecyl, 2-phenylpropyl and polyether (10 moles of ethylene oxide unit) functionalities, was taken. The fluid was stirred with an overhead stirrer at 2000 rpm. To this stirring liquid, 30 g of deionized water (50% water content for the end composition) was added very slowly, over a period of 35 minutes. The milky white emulsion was optionally homogenized with a T25 UltraTurrax for 2 minutes at 8000 rpm. A smooth, creamy, white, water-in-oil type emulsion resulted that was stable against separation at room temperature for more than six months. The emulsion was also stable against separation after centrifugation for 2 hours at 4000 rpm. The emulsion cannot be diluted with water but can be diluted with non-polar solvents such as isododecane. Average particle size measured with a Malvern Zetasizer instrument was approximately 303 nm. The emulsion was shear thinning. The emulsion was stable even when the water content was raised to 60%.

Example 4

With a procedure similar to that of Example 3, but with a mixing temperature of 75° C. instead of room temperature, the fluid of Example 2 with octadecyl, 2-phenylpropyl and polyether (10 moles of ethylene oxide unit) functionalities, formed a clear gel-like W/O emulsion. The emulsion was stable against separation for over one month. Average particle size measured with a Malvern Zetasizer instrument was approximately 96 nm A stable emulsion could also be made with this fluid with water content as high as 80% by mixing at room temperature.

Comparative Example C5

The procedure as described in Example 3 was repeated with $(M^{Ar})_2(M^R)_2Q$ (where Ar=2-phenylpropyl, R=n-octadecyl, $C_8H_{17}$), which is a branched siloxane having only 2-phenylpropyl and octadecyl functionalities but no polyether functionality. No stable emulsion was formed. The milky white mixture separated into two different phases within 2 hours.

Example 6

The W/O emulsion of silicone (0.3 mL) prepared according to the procedure described in Example 3 was applied to a 304 brushed stainless steel panel and spread with a cotton diaper material to fill to an area of 3"×4" on the panel. Next to this area, 0.3 mL of a Weiman Stainless Steel cleaner and polish, which is a leading stainless steel surface care brand in the market, was applied in a similar manner. The W/O emulsion coated area showed a more visual, darker polish effect compared to both the untreated and the Weiman treated areas of the steel surface. Moreover, the W/O emulsion coated area demonstrated a distinctively better resistance to fingerprints and smudge and a slightly better gloss (6.0 gloss unit vs. 4.6), measured at 85 degree angle with a gloss meter, compared to the Weiman coated area. Also, the coated surface showed good dust resistance. It can be anticipated that the W/O emulsion could be useful in other surface care applications such as wood polish, car wax, tire shine, leather polish/shine etc.

Example 7

Inside a Plexiglass chamber, a glass panel (12.8 cm×7.5 cm) was mounted vertically at a distance of 14 cm from the nozzle of a Safetylst Ultrasonic Humidifier filled with deionized water. The humidifier was turned on at its maximum capacity. The humidifier created a visible stream of vapor that flowed directly on the glass panel and quickly filled the chamber. A glass panel without any additional coating fogged up in approximately 2 minutes whereas a glass panel coated with the W/O emulsion prepared according to the procedure described in Example 3 stayed fog free for more than 4.5 hours.

Example 8

A lipgloss formulation was made with the emulsion from Example 3 according to the following composition:

| Phase | INCI Name | Trade Name | Manufacturer | Amount (g) |
|---|---|---|---|---|
| A | Diethylhexyl Carbonate | Tegosoft DEC | Evonik | 7.4 |
|  | Isopropyl Myristate | HallStarIPM-NF | HallStar | 7 |
|  | Isostearyl Alcohol | Prisorine 3515 | Croda | 7.5 |
|  | Polyphenylsilsesquioxane | BELSIL SPR 45 VP | Wacker Chemie AG | 3 |
| B | Flavor | Peppermint Oil | Spectrum Chemical | 0.13 |
|  | C26-28 Alkyl Dimethicone | BELSIL CDM 3526 VP | Wacker Chemie AG | 7 |
|  | Microcrysalline Wax | Paracera M | Koster& Keunen LLC | 1.5 |
|  | Ozokerite | Ozokerit 6001 | Frank B Ross Co | 2.3 |
|  | Emulsion from Example 1 (50% silicone active) | — | — | 14 |
|  | Mica & Titanium Dioxide | Timiron Diamond Cluster MP-149 | Rona | 0.25 |

Components of phase A were mixed until homogenous at 90° C. Then the components of phase B were added one after the other and mixed until the mixture was homogeneous. The mixture was cooled to room temperature.

The lip gloss composition showed a distinctive gloss on skin. Also, it provided a nonsticky and light feel and demonstrated good spreadability on the skin.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An external-surfactant-free water-in-oil invert emulsion, comprising:
    A) from 5 to 95 parts by weight of one or more self-emulsifying organopolysiloxanes of the formulae (i) and (ii):
        (i) a liquid, branched organopolysiloxane of the formula $$M_a T_b Q_c$$

where a is at least 3, b is 0-4, and c is 0-2;
where M is a monovalent siloxy unit of the formula $$R_e R^1_f R^2_g R^3_h SiO_{(4-(e+f+g+h))/2}$$

where e, f, g, and h are individually integers from 0 to 3 and the sum (e+f+g+h) equals 3;
R is a lower alkyl group or an aryl group,
$R^1$ is an aralkyl group
$R^2$ comprises an alkylene-bonded surfactant group selected from the group consisting of polyoxyalkylene polyethers, polyhydroxyl compounds, and saccharides,
$R^3$ is a long chain alkyl group;

where T is a trivalent siloxy unit of the formula $$R_{e'} R^1_{f'} R^2_{g'} R^3_{h'} SiO_{(4-(e'+f'+g'+h'))/2}$$

where the sum (e'+f'+g'+h') is 1;
where Q units are of the formula $SiO_{4/2}$,
and the liquid, branched organopolysiloxane contains at least one of each of $R^1$, $R^2$, and $R^3$;
        (ii) a liquid organopolysiloxane comprising groups of the formula:

$$R'_3 SiO, (R^{1'}_2 SiO)_w, (R^{1'} JSiO)_x, (R^{1'} KSiO)_y, (R^{1'} LSiO)_z, \text{ and } SiR'_3$$

wherein
R' is a group L or a $C_{1-30}$ hydrocarbon group, one R' of the $R_3SiO$— or —$SiR'_3$ group is optionally a hydroxyl group, and one or more R' of the $R_3SiO$— or —$SiR'_3$ group is/are optionally a $C_{1-8}$ alkoxy group;
$R^{1'}$ is hydrogen or a $C_{1-30}$ hydrocarbon group;
J is an aralkyl group;
K is a long chain $C_{8-45}$ alkyl group;
L is an Si—C bonded, oxygen-containing hydrophilic group having a molecular weight greater than 100 Daltons;
w is from 0 to 200;
x is from 1-100;
y is from 1 to 50; and
z is from 1 to 50, containing less than 5 mol percent, based on the total mols of w,x,y, and z, of $R'SiO_{3/2}$ groups and $SiO_{4/2}$ groups which form branching sites, wherein the refractive index of the liquid organopolysiloxane (ii) is at least 1.45, and
    B) water.

2. The external-surfactant-free water-in-oil invert emulsion of claim 1, wherein the self-emulsifying organopolysiloxanes is one of formula (i).

3. The external-surfactant-free water-in-oil invert emulsion of claim 1, wherein the self-emulsifying organopolysiloxanes is one of formula (ii).

4. The external-surfactant-free water-in-oil emulsion of claim 1, which has shear-thinning properties.

5. A composition for surface care application comprising an external-surfactant-free water-in-oil invert emulsion described in claim 1, which provides good shine and shows good smudge resistance.

6. An antifog coating composition comprising an external-surfactant-free water-in-oil emulsion of claim 1.

7. A cosmetic or hair care composition comprising an external-surfactant-free water-in-oil invert emulsion of claim 1.

8. An external-surfactant-free water-in-oil invert emulsion of claim 1, which has low cyclic silicone content.

9. An external-surfactant-free water-in-oil invert emulsion of claim 1, which is prepared without application of high shear.

10. An external-surfactant-free water-in-oil invert emulsion described in claim 1, which is prepared at room temperature without application of heat.

11. An external-surfactant-free water-in-oil invert emulsion described in claim 1, which has an average particle size less than 100 nm.

12. A process for forming an external-surfactant-free water-in-oil invert emulsion of claim 1, comprising adding an aqueous phase to at least one organopolysiloxane of formulae i) and ii) with stirring.

* * * * *